United States Patent
Sugasawa et al.

(10) Patent No.: US 7,090,989 B2
(45) Date of Patent: Aug. 15, 2006

(54) RECOMBINANT HUMAN SM-11044-BINDING RECEPTOR PROTEINS EXHIBITING LIGAND-BINDING ACTIVITIES, AND THEIR USES

(75) Inventors: Toshinari Sugasawa, Takatsuki (JP); Jun Hidaka, Toyonaka (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 380 days.

(21) Appl. No.: 10/755,466

(22) Filed: Jan. 13, 2004

(65) Prior Publication Data

US 2004/0265854 A1   Dec. 30, 2004

Related U.S. Application Data

(62) Division of application No. 09/786,681, filed on Apr. 30, 2001, now Pat. No. 6,692,926.

(30) Foreign Application Priority Data

Sep. 8, 1998   (JP) ................................ 10-253771

(51) Int. Cl.
| | |
|---|---|
| *G01N 33/567* | (2006.01) |
| *C07K 1/00* | (2006.01) |
| *C07H 21/04* | (2006.01) |
| *C12N 1/20* | (2006.01) |
| *C12P 21/02* | (2006.01) |

(52) U.S. Cl. .................. 435/7.21; 435/6; 435/69.1; 435/252.3; 435/320.1; 424/9.1; 424/9.2; 436/501; 530/350; 536/23.5

(58) Field of Classification Search .................. None
See application file for complete search history.

(56) References Cited

FOREIGN PATENT DOCUMENTS

WO    WO 9826065 A1   6/1998

OTHER PUBLICATIONS

Sugasawa, Toshinari et al., The Journal of Biological Chemistry, vol. 272, No. 34, pp. 21244-21252. (1997).
Sambrook et al., Molecular Cloning, pp. 8.11-8.30, (1989).
Myer et al., EMBO J., vol. 16, No. 8 pp. 2130-2139, (1997).
Bonin et al., Gene, vol. 14, pp. 75-77, (1994).

*Primary Examiner*—Elizabeth Kemmerer
*Assistant Examiner*—Michael Brannock
(74) *Attorney, Agent, or Firm*—Birch, Stewart, Kolasch & Birch, LLP

(57) ABSTRACT

Transformed cells designed to express a recombinant human SMBP at an elevated level to the extent that its ligand-binding activity can be measured, and cellular membrane fractions thereof; recombinant human SMBPs isolated from the transformed cells or the cellular membrane fractions thereof; a screening system for human SMBP agonists/antagonists characterized by utilizing the transformed cells, the cellular membrane fractions thereof or the isolated recombinant human SMBPs; and human SMBP agonists or antagonists obtainable by the screening system, are provided by deleting the polythymidine sequence from the base sequence of the 3'-untranslated region.

1 Claim, 1 Drawing Sheet

US 7,090,989 B2

RECOMBINANT HUMAN SM-11044-BINDING RECEPTOR PROTEINS EXHIBITING LIGAND-BINDING ACTIVITIES, AND THEIR USES

This application is a Divisional of application Ser. No. 09/786,681, filed on Apr. 30, 2001 now U.S. Pat. No. 6,692,926, the entire contents of which are hereby incorporated by reference and for which priority is claimed under 35 U.S.C. § 120; and this application claims priority of Application No. 253771/1998 filed in Japan on Sep. 8, 1998, under 35 U.S.C. §119.

TECHNICAL FIELD

The present invention relates to recombinant human SM-11044 ((L)-threo-3-(3,4-dihydroxyphenyl)-N-[3-(4-fluorophenyl)propyl] serine pyrrolidine amide hydrobromide)-binding receptor proteins exhibiting ligand-binding activities (abbreviated as SMBP hereinafter), and their uses. More particularly, it relates to transformed cells that are designed to express a recombinant human SMBP at an elevated level to the extent that its ligand-binding activity can be measured by deleting the polythymidine sequence from the base sequence of the 3'-untranslated region, and cellular membrane fractions thereof, to recombinant human SMBPs isolated from the transformed cells or the cellular membrane fractions thereof, to a screening system for discovering human SMBP agonists/antagonists characterized by utilizing the transformed cells, the cellular membrane fractions thereof or the isolated recombinant human SMBPs, and to human SMBP agonists or antagonists obtainable by the screening system.

BACKGROUND ART

SM-11044 ((L)-threo-3-(3,4-dihydroxyphenyl)-N-[3-(4-fluorophenyl)propyl] serine pyrrolidine amide hydrobromide)-binding receptor protein (SMBP) was discovered as a new protein that is bound by SM-11044, which is an agonist for $\beta$-adrenergic receptors, and by iodocyanopindolol, which is an antagonist for $\beta$-adrenergic receptors (Sugasawa, T. et al., J. Biol. Chem., 272, 21244–21252 (1997)). SMBP is a membrane protein resided at lung, ileum, and eosinophil membrane, and is believed to act as a receptor for SM-11044. SM-11044 was known to have activities to down-regulate the depolarization-mediated contraction of intestine and to inhibit migration of eosinophils, and has been believed to exert such SM-11044's functions via SMBP (Sugasawa, T. et al., J. Biol. Chem., 272, 21244–21252 (1997)).

Although the cDNA of a human SMBP was recently cloned (International Publication No. WO 98/26065), it was not reported that SM-11044 binds to any recombinant protein translated from the cDNA. In other words, there has been no report showing that a human SMBP is expressed at an elevated level to the extent that its ligand-binding activity can be measured, and, therefore, any SMBP has not yet been established in its particular availability.

DISCLOSURE OF THE INVENTION

The present invention aims to provide a recombinant human SMBP exhibiting ligand-binding activities, and its use. More particularly, it aims to provide transformed cells that are designed to express a recombinant human SMBP at an elevated level to the extent that its ligand-binding activity can be measured by deleting the polythymidine sequence from the base sequence of the 3'-untranslated region, cellular membrane fractions thereof, and recombinant human SMBPs isolated from the transformed cells or the cellular membrane fractions thereof, as well as a screening system for discovering human SMBP agonists/antagonists characterized by utilizing the transformed cells, the cellular membrane fractions thereof or the isolated recombinant human SMBPs, and human SMBP agonists or antagonists obtainable by the screening system.

As mentioned above, SMBP has been believed to be a receptor that mediates actions to down-regulate the depolarization-mediated contraction of intestine and to inhibit migration of eosinophils. Accordingly, it is expected that substances exhibiting an agonistic activity for SMBP would bind to SMBP to exert the functions as mentioned above, thereby leading to pharmaceutical compositions for treating inflammatory diseases involving eosinophil infiltration, asthma, or bowel diseases.

The present inventors attempted to construct a screening system for discovering efficiently ligands binding to SMBP, which comprises using SMBP in view of the development of such pharmaceutical compositions. International Publication No. WO 98/26065 describes that western blotting with use of anti-human SMBP antibody revealed that a SMBP protein was expressed by COS cells transformed with the recombinant human SMBP cDNA. However, the SMBP protein was expressed in a quite small amount, and, consequently, it has not been reported that any human SMBP is expressed in a sufficiently high level to construct screening systems. In fact, the inventors obtained the relevant human SMBP cDNA fragment (SEQ ID NO: 1) from the applicant of the International Application (WO 98/26065), Vetigen, and transformed the cDNA into COS-1 cells or CHO-K1 cells. Then, the inventors determined a ligand-binding activity of the transfectants, but found no activity. Due to these facts, the inventors believed either of 1) that any protein had not translated from the human SMBP cDNA, or 2) that, even if a protein was translated, it had not been expressed at an elevated level to the extent that its ligand-binding activity can be measured.

The present inventors presumed that drawbacks involving the structure of the cDNA would cause no or little expression of the protein. Restudy of the base sequence of SEQ ID NO: 1 revealed that the 3'-untranslated region contains a polythymidine sequence consisting of a consecutive sequence of as many as 37 thymidines, and that the polyuridine sequence of the mRNA corresponding to the polythymidine sequence binds to the polyadenine tail (poly-A) residing at the 3'-terminus of the SMBP mRNA to form certain secondary structure, which would thereby restrain translation into proteins.

On the basis of the above presumption, by deleting the polythymidine sequence from the 3'-untranslated region in the base sequence of the human SMBP cDNA depicted in SEQ ID NO: 1, the inventors have successfully expressed a recombinant human SMBP at an elevated level to the extent that its ligand-binding activity can be measured for the first time. Further, the inventors have successfully established, for the first time, a screening system for discovering SMBP agonists/antagonists that are effective in a human, owing to the availability of such measurement of ligand-binding activity.

The present invention has been completed on the basis of the findings as described above.

Thus, the present invention relates to:

(1) A process for expressing a recombinant protein at an elevated level, which comprises deleting a sequence comprising the polythymidine sequence from the base sequence of the 3'-untranslated region;

(2) A process for expressing a recombinant human SMBP at an elevated level, which comprises;

(a) preparing a DNA wherein a sequence comprising the polythymidine sequence is deleted from the 3'-untranslated region in the base sequence of SEQ ID NO: 1;

(b) introducing the DNA of the above (a) into an expression vector;

(c) transforming a host cell with the expression vector of the above (b); and (d) culturing the transformed cells of the above (c) under an appropriate condition;

(3) A DNA encoding a recombinant human SMBP, which is characterized in that;

(e) a sequence comprising the polythymidine sequence is deleted from a 3'-region from position 1875 in the base sequence of SEQ ID NO: 1; and (f) the recombinant human SMBP that is a translation product of the DNA can be expressed at an elevated level to the extent that its ligand-binding activity can be measured;

(4) The DNA of the above (3) wherein a sequence comprising all or part of the base sequence from positions 1899 to 1935 of SEQ ID NO: 1 is deleted;

(5) The DNA of the above (4) wherein the portion of the base sequence from positions 1875 to 2072 of SEQ ID NO: 1 is deleted.

(6) The DNA of the above (5), which consists of the base sequence of SEQ ID NO: 3.

(7) An expression vector which carries the DNA of any one of the above (3) to (6).

(8) A transformed cell expressing a recombinant protein at an elevated level to the extent that its ligand-binding activity can be measured, which is obtainable by the process of the above (1) or (2), or a cellular membrane fraction thereof.

(9) A transformed cell expressing a recombinant human SMBP at an elevated level to the extent that its ligand-binding activity can be measured, which is obtainable by the process of the above (2), or a cellular membrane fraction thereof.

(10) The transformed cell of the above (9), which is obtainable by culturing cells transformed with the expression vector of the above (7) under an appropriate condition, or a cellular membrane fraction thereof.

(11) A process for preparing a recombinant human SMBP, which comprises isolating the recombinant human SMBP from the transformed cells or the cellular membrane fractions thereof according to the above (9) or (10).

(12) A recombinant human SMBP obtainable by the process of the above (11).

(13) A screening system for discovering a human SMBP agonist or antagonist, which comprises utilizing the transformed cell or the cellular membrane fraction thereof according to the above (9) or (10), or the recombinant human SMBP of the above (12).

(14) A human SMBP agonist or antagonist obtainable by the screening system of the above (13).

(15) A pharmaceutical composition for inhibiting migration of eosinophils, or for relaxing the contraction of intestine, which comprises the agonist of the above (14).

According to the present invention, a recombinant human SMBP has been successfully expressed at an elevated level to the extent that its ligand-binding activity can be measured, by deleting the polythymidine sequence from the 3'-untranslated region of the DNA encoding the human SMBP. It is understood that this would result from the consequence of the right translation into a protein provided by deletion of the polythymidine sequence that restrains the translation into a protein due to certain secondary structure formed by binding the polyuridine sequence in the mRNA corresponding to the polythymidine sequence to the polyadenine tail (poly-A) residing at the 3'-terminus of the mRNA.

Besides the human SMBP DNA as shown above, it is believed that similar effects can be also obtained by deleting a polythymidine sequence in cases of DNAs of other recombinant proteins having a polythymidine sequence in the 3'-regions. Accordingly, the present invention provides a process for expressing recombinant proteins in general at elevated levels, as well as transformed cells expressing recombinant proteins obtainable by the process, and the cellular membrane fractions thereof.

Particular steps of the process for conducting the elevated expression as mentioned above are provided below, taking a recombinant human SMBP for instance. Thus, the process for expressing a recombinant human SMBP at an elevated level comprises;

(a) preparing a DNA wherein a sequence comprising the polythymidine sequence is deleted from the 3'-untranslated region in the base sequence of SEQ ID NO: 1;

(b) introducing the DNA of the above (a) into an expression vector;

(c) transforming a host cell with the expression vector of the above (b); and (d) culturing the transformed cells of the above (c) under an appropriate condition. Details of each step of these (a) to (d) are described hereinafter.

In the present invention, the term "DNA" refers to any DNA as long as the DNA encodes a recombinant human SMBP, of which the polythymidine sequence is deleted from the 3'-untranslated region in the base sequence of SEQ ID NO: 1. Specific examples include a DNA encoding a recombinant human SMBP, which is characterized in that; (a) a sequence comprising the polythymidine sequence is deleted from a 3' region from position 1875 in the base sequence of SEQ ID NO: 1; and, as a consequence of the deletion, (b) the translation product of the DNA, the recombinant human SMBP, may be expressed at an elevated level to the extent that its ligand-binding activity can be measured.

In this context, "a DNA encoding human SMBP" may be readily cloned on the basis of the base sequence of human SMBP described in WO 98/26065 by using as PCR primers or probes for hybridization an appropriate portion in the base sequence according to conventional methods (consulting a standard text such as "Molecular Cloning", 2nd ed., Cold Spring Harbor Laboratory Press (1989)). Further, alterations such as substitution, deletion, or addition may be also made to the cloned DNA according to "Molecular Cloning" 2nd Edt. Chapter 15, Cold Spring Harbor Laboratory Press (1989), and such altered SMBPs-encoding DNAs fall within the scope of the DNA encoding a recombinant -human SMBP of the present invention as long as the expressed products of the DNAs, altered SMBPs, exhibit a binding activity to ligands such as SM-11044.

Among these DNAs encoding recombinant human SMBPs, specific examples of the present invention include a DNA which is characterized in that; (a) a sequence comprising the polythymidine sequence is deleted from a 3' region from position 1875 in the base sequence of SEQ ID NO: 1; and (b) the translation product of the DNA, the recombinant human SMBP, may be expressed at an elevated level to the extent that its ligand-binding activity can be measured.

In this connection; with respect to the base sequence up to position 1875 in the sequence of human SMBP-DNA of SEQ ID NO: 1, the base sequence up to position 1875 in the sequence of SEQ ID NO: 1, or a sequence wherein the sequence contains the above alteration in said base sequence, and the expressed product of the DNA, a recombinant SMBP, exhibits a binding activity to ligands such as SM-11044 are fallen within the scope of the present invention. Specific examples include the sequence up to position 1874 in SEQ ID NO: 1, the sequence up to position 1827 in SEQ ID NO: 3, and the like.

With respect to a 3' region from position 1875 in the base sequence of SEQ ID NO: 1, any DNA wherein a sequence comprising a polythymidine sequence expected to inhibit the expression of a human SMBP protein is deleted falls within the scope of the present invention. Methods for deleting a sequence comprising the polythymidine sequence include a method for the deletion wherein suitable restriction enzyme sites positioned at each side of the polythymidine are utilized if any, and a method for the deletion involving well-known techniques such as PCR (Molecular Cloning: A Laboratory Manual 2nd Edt. Chapters 1–3, Cold Spring Harbor Laboratory Press (1989)).

In this connection, the term "polythymidine sequence" refers to a sequence comprising consecutive thymidines, of which the deletion leads to the expression of the translation product, the recombinant human SMBP, at an elevated level to the extent that its ligand-binding activity can be measured.

Examples of the method for measuring a ligand-binding activity include the method described in J. Biol. Chem., 272, 21244–21252 (1997). The method in principle comprises determining a binding reactivity to 1 nM [$^{125}$I]-iodocyanopindolol used as a ligand, determining a nonspecific binding reactivity of iodocyanopindolol by use of $10^{-4}$ M SM-11044, and subtracting the nonspecific binding reactivity from the binding reactivity so as to measure a ligand-binding activity of SMBP protein (J. Biol. Chem., 272, 21244–21252 (1997)).

Specifically, a human SMBP expression vector is prepared by introducing a candidate DNA for the DNA of the present invention into an expression vector, and a transformed cell is prepared by introducing the SMBP expression vector into a host cell. Then, the resultant transformed cells or cellular membrane fractions thereof are subjected to the system for measuring a ligand-binding activity as shown above (the expression vector, the transformed cells, and the cellular membrane fractions thereof are further described hereinafter). Examples of the method for measuring a ligand-binding activity include the substantially same method as that described in J. Biol. Chem., 272, 21244–21252 (1997) mentioned above, and a method that is detailed in Example 6. Specifically, a 96-well Multiscreen plate (Millipore) in which a piece of glass fiber paper is placed on the bottom of the wells is treated with Tris-HCl buffered saline containing 0.3% polyethyleneimine (Sigma) (reconstituted to pH7.4 with 6N HCl), and washed by vacuum filtration with Tris-HCl buffered saline (pretreatment). Then, 200 μl of Tris-HCl buffered saline containing 1 nM [$^{125}$I]-iodocyanopindolol (Amersham) and a cellular membrane fraction as mentioned above (50 μg of membrane protein) that have been incubated at 37° C. for 30 minutes is added to each well on the 96-well Multiscreen plate, and are washed by vacuum filtration. The cellular membrane fraction is harvested on the glass fiber paper, and washed by vacuum filtration with 200 μl of an ice-cooled Tris-HCl buffered saline. Then, the amount of [$^{125}$I]-iodocyanopindolol bound to the membrane fraction trapped on the paper is determined by a gamma counter to represent a total binding. Nonspecific binding of [$^{125}$I]-iodocyanopindolol is determined by conducting an incubation as mentioned above in the presence of $10^{-4}$ M SM-11044 (Sumitomo Pharmaceuticals Co., Ltd. it can be prepared according to the process described in Japanese Patent Publication (kokai) No. 132935/1985, Japanese Patent Publication (kokoku) No. 50499/1993) and then conducting similar procedures to those mentioned above. A ligand-binding to SMBP may be calculated by subtracting the nonspecific binding from the total binding.

DNAs of the present invention can be readily selected by subjecting transformed cells introduced with a candidate DNA for the DNA of the present invention, or cellular membrane fractions thereof to the system for measuring a ligand-binding activity as shown above. The system for the measurement may be appropriately modified as far as the common knowledge of those skilled in the art. For example, SM-11044, BRL-35135A (Smith Kline Beecham), or alprenolol (Ciba Geigy) labeled with [$^{125}$I] or [$^3$H] may be used instead of [$^{125}$I]-iodocyanopindolol.

Among the DNAs of the present invention, suitable examples include a DNA wherein a sequence comprising all or part of the polythymidine sequence residing from positions 1899 to 1935 is deleted from the 3'-untranslated region in the base sequence of SEQ ID NO: 1. In this connection, "the part" is preferably about 30 bases in length since it should have been bound to the polyadenine tail (poly-A) attached to the 3'-terminus of the SMBP mRNA to form certain secondary structure, although any length in the part may be acceptable as long as a recombinant human SMBP can be expressed at an elevated level to the extent that its ligand-binding activity can be measured.

More suitable examples of the DNA of the present invention includes a DNA wherein the sequence from positions 1875 to 2072 is deleted from the base sequence of SEQ ID NO: 1, and even more suitable examples include the human SMBP DNA consisting of the base sequence of SEQ ID NO: 3.

The DNA of the present invention as mentioned above may be incorporated into an expression vector according to conventional methods to obtain a SMBP expression vector carrying the DNA of the invention.

In this connection, the expression vectors to be incorporated with the DNA of the present invention may be any vector capable of expressing efficiently the subject in a host cell, and preferably include a pcDNA3.1 derivative, pRc/RSV, pRc/CMV, a pEF derivative (all of them are from Invitrogen), pIRESneo (Clontech), and a pREP9 derivative (Invitrogen).

The SMBP expression vector thus prepared may be transformed into host cells to prepare transformed cells wherein the expression vector of the present invention is retained stably in chromosomes of the host cells. In this connection, host cells may be any cell as long as a foreign gene may be stably integrated into chromosomes of the host cells, and mammal cells are preferred. Examples of the host cells include CHO cells, L929 cells, C127 cells, and BALB/c3T3 cells as well as variants thereof wherein a dihydrofolate reductase or thymidine kinase function is defective.

Examples of methods for transforming the expression vector of the present invention into host cells include the calcium phosphate method (J. Virol.,52, 456–467 (1973)), a method involving LT-1 (Panvera), and a method involving lipids for gene-introduction (Lipofectamine, Lipofectin; Gibco-BRL). After the transformation, the cells may be cultured in a conventional medium containing a selective marker (for example, Zeocin in the case of using pcDNA3.1/Zeo(+) shown above as an expression vector) to select the transformed cells wherein the expression vector of the present invention is stably retained in chromosomes of the host cells.

The transformed cells thus obtained may be continuously cultured under an appropriate condition to prepare transformed cells of the present invention wherein a recombinant human SMBP is expressed on the cellular membrane at an elevated level to the extent that its ligand-binding activity can be measured.

The term "appropriate condition" refers to a condition wherein a cultivation is conducted at 37° C. under 5% $CO_2$ in a culture medium suitable for respective host cell, and examples include a condition wherein CHO cells are cultured at 37° C. under 5% $CO_2$ in HAM'S F-12 medium containing 10% bovine calf serum.

Cellular membrane fractions of the present invention can be prepared from the transformed cells thus obtained wherein a human SMBP is expressed at an elevated level. For example, a process for preparing the cellular membrane fractions may comprise adding to the cells a hypotonic homogenate buffer (10 mM Tris-HCl buffer, 1 mM EDTA, 0.5 mM PMSF or 1 mM AEBSF, 5 μg/ml aprotinin, 5 μg/ml leupeptin, pH7.4), allowing the mixture to stand at 4° C. for about 30 minutes so as to destroy the cells due to the hypotonic condition, homogenizing it by the pipetting, and centrifuging the homogenate at 4° C. at 50000×g for about 30 minutes, thereby obtaining the cellular membrane fractions of the present invention.

Alternatively, for example, the method described by F. Pietri-Rouxel et al. (*Eur. J. Biochem.*, 247, 1174–1179 (1997)) may be used to prepare the cellular membrane fractions of the present invention.

A recombinant human SMBP of the present invention can be isolated from the transformed cells of the cellular membrane fractions of the present invention thereof thus obtained. Specifically, for example, the method of R. G. Shorr, et al. (*Proc. Natl. Acad. Sci. USA*, 79, 2778–2782 (1982); *J. Biol. Chem.* 257, 12341–12350 (1982)) may be used to obtain a crude extract of a human SMBP of the present invention. Further, a method for purifying a human SMBP from the crude extract is exemplified by the method of J. L. Benovic, et al. (*Biochem.*, 23, 4510–4518 (1984)).

Specific examples of the recombinant human SMBP of the present invention include a human SMBP consisting of the amino acid of SEQ ID NO: 2 or SEQ ID NO: 4, and a altered SMBP consisting of said amino acid that contains substitution, deletion, and/or addition is also fallen within the scope of the recombinant human SMBPs of the present invention as long as the latter has a binding activity to ligands such as SM-11044.

Agonists or antagonists binding to the human SMBP can be screened by use of either of the transformed cells expressing the recombinant human SMBP at an elevated level, the cellular membrane fractions thereof, or the isolated recombinant human SMBP, each of which are as obtained above.

The screening by use of the cellular membrane fractions of the transformed cells expressing the recombinant human SMBP at an elevated level may be conducted for example by the following method.

First of all, a Tris-HCl buffered saline containing the cellular membrane fraction of the present invention (50–200 μg membrane protein) and 1 nM [$^{125}$I]-iodocyanopindolol is incubated at 37° C. for 30 minutes, and the reaction is added to each well on a 96-well Multiscreen plate that has been treated by a similar pretreatment to that in "the method for measuring a ligand-binding activity" as mentioned above, then being aspirated by vacuum filtration. Subsequently, a similar treatment to that in "the method for measuring a ligand-binding activity" as mentioned above is conducted, and the amount of [$^{125}$I]-iodocyanopindolol bound to the membrane fraction trapped on the paper is determined by a gamma counter to give a binding, which represents binding A. Then, the incubation as shown above is conducted in the presence of a test compound at a normal range of concentrations ($10^{-12}$–$10^{-4}$M), and then a similar procedure is conducted to give a binding, which represents binding B. A binding that is provided by use of $10^{-4}$M SM-11044 instead of a test compound represents binding C. Accordingly, when the value subtracted binding B from binding A is equivalent to one subtracted binding C from binding A, the test compound is estimated to have 100% SMBP-binding activity, and, when the value is the half, the compound is estimated to have the 50%. SMBP ligands thus selected are subjected to an assay as described in either *J. Biol. Chem.*, 272, 21244–21252 (1997), *Eur. J. Pharmacol.* 216, 207–215 (1992), or *Agents Actions* 37, 233–237 (1992). At that time, when down-regulating the contraction of intestine or inhibiting the migration of eosinophils equivalently to or more than SM-11044, the ligands may be a SMBP agonist, whereas when showing the inverse activities, they may be a SMBP antagonist.

The screening by use of the transformed cells expressing the human SMBP of the present invention at an elevated level may be conducted for example by the following method.

First of all, the transformed cells expressing the human SMBP of the present invention at an elevated level that have been washed with Dulbecco's phosphate buffered saline (Gibco) are incubated with 1–5 mM EDTA-Dulbecco's phosphate buffered saline at room temperature, and then removed from the culture dish. After centrifuged (400×g, 10 min, 4° C.) and the supernatant being removed by aspiration, the cells are suspended by the pipetting in Tris-HCl buffered saline containing 0.2% bovine serum albumin. The cells at $5 \times 10^5$, 1 nM [$^{125}$I]-iodocyanopindolol, and Tris-HCl buffered saline containing 0.2% bovine serum albumin are incubated at 37° C. for 30 minutes, and the reaction is added to each well on a 96 well-Multiscreen plate that has been treated by a similar pretreatment to that in "the method for measuring a ligand-binding activity" as mentioned above, the being aspirated by vacuum filtration. Subsequently, a similar treatment to that in "the method for measuring a ligand-binding activity" as mentioned above is conducted, and the amount of [$^{125}$I]-iodocyanopindolol bound to the membrane fraction trapped on the paper is determined by a gamma counter to give a binding, which represents binding A. Then, incubation as shown above is conducted in the presence of a test compound at a normal rage of concentrations ($10^{-12}$–$10^{-4}$M), and a similar procedure is conducted to give a binding, which represents binding B. A binding that is provided by use of $10^{-4}$M SM-11044 instead of a test compound represents binding C. Subsequent procedures for the estimation are as shown above.

The screening by use of the recombinant human SMBP isolated from the transformed cells or the cellular membrane fractions thereof according to the present invention may be conducted for example by the following method.

First of all, an isolated SMBP standard is prepared by solubilizing the transformed cells or the cellular membrane fractions thereof by use of a suitable solubilizer, preferably, β-D-octylglucoside. Two hundreds fifty μl of Tris-HCl buffered saline containing the isolated SMBP standard and 1 nM [$^{125}$I]-iodocyanopindolol is incubated at 37° C. for 30 minutes, and then 250 μl of an ice-cooled Tris-HCl buffered saline is added thereto, thereby quenching the reaction. The reaction is applied to Sephadex G-50 column (Pharmacia) that have been equilibrated with Tris-HCl buffered saline, and eluted with Tris-HCl buffered saline. The amount of [$^{125}$I]-iodocyanopindolol bound to the SMBP fraction thus isolated by the gel filtration is determined by a gamma counter to give a binding, which represents binding A. Subsequently, incubation as shown above is conducted in the presence of a test compound at a normal rage of concentrations ($10^{-12}$–$10^{-4}$M), and a similar procedure is conducted to give a binding, which represents binding B. A binding that is provided by use of $10^{-4}$M SM-11044 instead of a test compound represents binding C. Subsequent procedures for the estimation are as shown above.

The screening systems as described above can be modified as appropriate within the knowledge of those skilled in the art.

Human SMBP agonists obtainable by the above screening systems are useful for an agent for inhibiting migration of eosinophils, or relaxing the contraction of intestine, and, specifically, are useful as a medicament or prophylactic for inflammatory diseases, asthma, or bowel diseases such as allergic gastrointestinal symptoms, involving eosinophil infiltration.

Agonists or antagonists obtainable by the screening systems of the present invention may be used for a pharmaceutical composition as shown above in accordance with conventional manners. For example, such substances can be administered orally in the form employed commonly in the art, such as tablets, capsules, syrups, suspensions, or the like. Such substances can also be administered parenterally in the form of, for example, solutions, emulsions, suspensions, or the like, as well as can be administered by rectal route in the form of suppositories. Such suitable dosage forms may be prepared in accordance with conventional manners by combining the active ingredient with conventional carriers, excipients, binders, stabilizing agents, or the like. Injectable formulations can additionally contain buffers, solubilizing agents, or isotonizating agents. Doses and frequencies vary depending on, for example, the disease and condition to be treated, the age and weight of a particular patient, a dosage form, and the like, and a typical daily dose for adults of active ingredients in case of oral formulations may range about 1 mg to about 1000 mg, preferably, about 10 to about 500 mg, which may be administered at a time or in portions. In case of the injectable formulations, a dose of active ingredients may range about 0.1 mg to about 500 mg, preferably, about 3 mg to about 100 mg, which may be administered at a time or in portions.

BEST MODE FOR CARRYING OUT THE INVENTION

Figure 1:
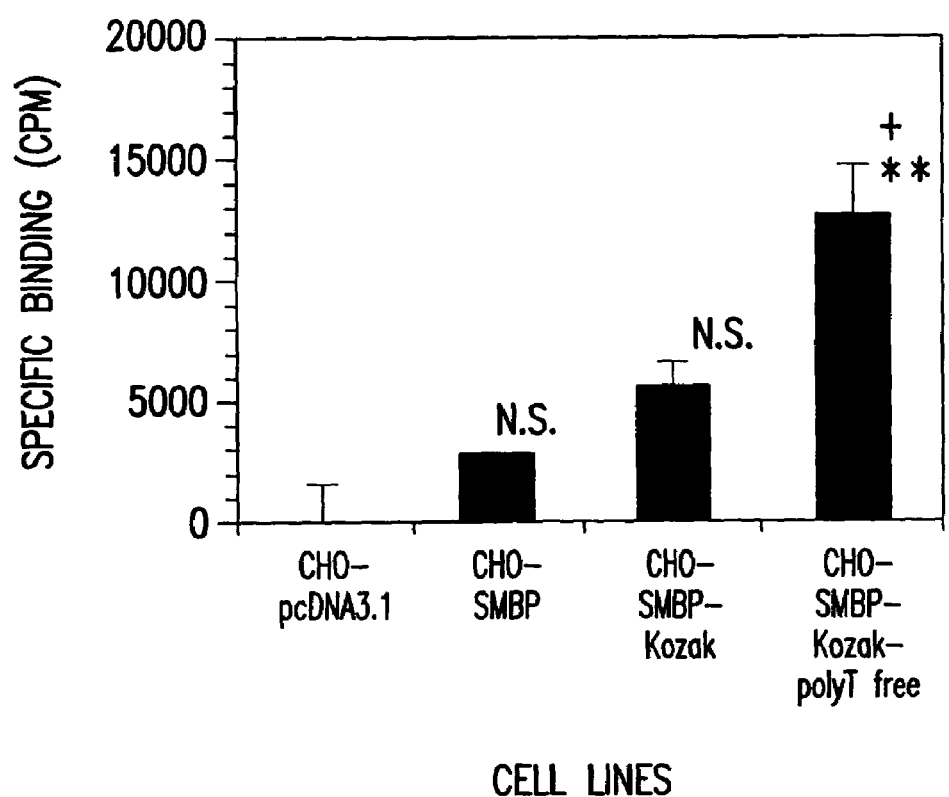
FIG. 1 is a graph showing the values of the ligand-binding activities that were measured using the cellular membranes of COS-7 cells transfected with pcDNA3.1/Zeo(+), SMBP-pcDNA3.1/Zeo(+), SMBP-Kozak-pcDNA3.1/Zeo(+), or SMBP-Kozak-pcDNA3.1/Zeo(+) poly-T free, wherein these are indicated by CHO-pcDNA3.1, CHO-SMBP, CHO-SMBP-Kozak, and CHO-SMBP-Kozak-poly T free, respectively. The results represent means ± standard error of the duplicate experiments. The axis of ordinates indicates the amounts (CPM) of [$^{125}$I]-iodocyanopindolol bound specifically to the SMBP. The symbols "**", "+", and "N.S." mean that there is a significant difference ($p<0.01$) in relation to CHO-pcDNA3.1, that there is a significant difference ($p<0.05$) in relation to CHO-SMBP, and that there is no significant difference in relation to CHO-pcDNA3.1 or CHO-SMBP, respectively.

The present invention is further illustrated by the following examples, but is not restricted by these examples in any way.

EXAMPLE 1

Introduction of BamHI/XbaI-Cleaved Fragment of SMBP-cDNA into Expression Vector

The BamHI/XbaI-cleaved fragment of SMBP-cDNA described in WO 98/26065 was obtained from the applicant of the patent application, Vetigen. The base sequence of the cDNA was sequenced by Takara Shuzo Co., Ltd. in accordance with a conventional method. The base sequence determined is shown in SEQ ID NO: 1, and the amino acid sequence of the protein encoded by the cDNA is shown in SEQ ID NO: 2. The base sequence of SEQ ID NO: 1 contains the base sequence disclosed as SEQ ID NO: 13 in WO 98/26065, and is further flanked by both 5' and 3' sequences.

Subsequently, the cDNA fragment was introduced into an expression vector, pcDNA3.1/Zeo(+) (Invitrogen), which had been cleaved with BamHI and XbaI, to give an expression plasmid, SMBP-pcDNA3.1/Zeo(+). E. coli JM 109 (Toyobo Co. Ltd.) was transformed with the plasmid SMBP-pcDNA3.1/Zeo(+), and cultured overnight on a LB plate containing 50 µg/ml ampicillin to give transformants. Plasmids prepared from the transformants according to a conventional procedure were cleaved with BamHI and XbaI to confirm that the SMBP-cDNA (about 2 kb) was inserted into the fragment. Further, cleavage with ApaI confirmed the orientation of the inserted sequence.

EXAMPLE 2

Binding of Kozak Sequence to SMBP-cDNA Fragment and Introduction into Expression Vector In surrounding sequences of ATG, a start codon, of the SMBP-cDNA fragment (at positions 49–51 in SEQ ID NO: 1), the Kozak's consensus sequence (ACCATGG SEQ ID NO:5) presumed to be necessary to translate efficiently mRNAs into proteins is not found. Accordingly, the surrounding sequence of the start codon of SMBP-cDNA fragment was replaced with ACCATGG (SEQ ID NO:5) as shown below in order to improve expression efficiency of proteins.

First, the following adapter containing the Kozak's consensus sequence and HindIII/NotI cleavage sites was prepared by annealing two types of different oligomers at 70° C. for 10 minutes:

Adapters Containing the Kozak's Sequence

```
5'-AGC TTC CAC CAT GGC-3'  (SEQ ID NO:6)

3'-AG GTG GTA CCG CCG G-5'  (SEQ ID NO:7)
```

The adapter thus prepared was incorporated into the expression vector pcDNA3.1/Zeo(+), which had been cleaved with HindIII/NotI to give a plasmid, Kozak-pcDNA3.1/Zeo(+). E. coli JM 109 was transformed with the plasmid Kozak-pcDNA3.1/Zeo(+), and cultured overnight on a LB plate containing 50 µg/ml ampicillin to give transformants. The multicloning sites in pcDNA3.1/Zeo(+)

contain a BamHI cleavage site between the HindIII-NotI sites, and, therefore, any plasmid without the inserted adapters would be cleaved with BamHI. Thus, the presence of the inserted adapters was determined by whether or not plasmids prepared from the transformants could be cleaved with BamHI.

Subsequently, the SMBP-cDNA fragment prepared by digesting the BamHI/XbaI-cleaved fragment of the SMBP-cDNA with NotI was introduced into Kozak-pcDNA3.1/Zeo(+), which had been cleaved with NotI, to give an expression plasmid, SMBP-Kozak-pcDNA3.1/Zeo(+). E. coli JM 109 (Toyobo Co. Ltd.) was transformed with the plasmid SMBP-Kozak-pcDNA3.1/Zeo(+), and cultured overnight on a LB plate containing 50 µg/ml ampicillin to give transformants. The plasmids prepared from the transformants were cleaved with HindIII and XbaI to confirm that the SMBP-cDNA (about 2 kb) was inserted into the plasmid. Further, cleavage with ApaI confirmed the orientation of the inserted sequence.

The amino acid sequence of the SMBP protein translated from the plasmid SMBP-Kozak-pcDNA3.1/Zeo(+) prepared as shown above was the sequence wherein the three amino acids at positions 2 to 4, His-Ala-Arg, is deleted from the amino acid sequence of SEQ ID NO: 2.

EXAMPLE 3

Deletion of Polythymidine Sequence from Expression Plasmid SMBP-Kozak-pcDNA3.1/Zeo(+), and Reintroduction into Expression Vector pcDNA3.1/Zeo(+)

A polythymidine sequence consisting of a consecutive sequence of 37 thymidines (poly-T) exists downstream of the stop codon (TAG) in the SMBP-cDNA, which sequence is between positions 1899–1935 in the base sequence of SEQ ID NO: 1. The inventors presumed that the poly-U in the mRNA corresponding to the poly-T should bind to the polyadenine tail (poly-A) residing at the 3'-terminus of the SMBP-mRNA to form certain secondary structure, which would destabilize the m-RNA, or block its transport through the nuclear membrane, thereby restraining translation into proteins. Thus, the base sequence downstream of position 1875 was excised from the base sequence of SEQ ID NO: 1 using restriction enzyme Ksp632I to give a SMBP-cDNA fragment wherein the portion of 198 bases containing the poly-T part was deleted, and the fragment was then introduced into an expression vector in accordance with the procedures as shown below.

Specifically, the expression plasmid SMBP-Kozak-pcDNA3.1/Zeo(+) as prepared in Example 2 was cleaved with Ksp632I to isolate a fragment (about 2.9 kb) wherein a SMBP-cDNA from which the portion of 198 bases containing the poly-T part was deleted, and a portion of pcDNA3.1/Zeo(+) were bound together. Then, the fragment was cleaved with HindIII, and a HindIII/Ksp632I-cleaved fragment of the SMBP-cDNA (about 1.8 kb) was isolated. The fragment was blunted with T4DNA polymerase (Takara Syuzo), and the blunt-ended fragment was introduced into an expression vector pcDNA3.1/Zeo(+) cleaved with EcoRV to give an expression plasmid SMBP-Kozak-pcDNA3.1/Zeo(+) poly-T free. The base sequence of the SMBP-cDNA carried on the expression plasmid SMBP-Kozak-pcDNA3.1/Zeo(+) poly-T free is shown in SEQ ID NO: 3, and the amino acid sequence thereof is shown in SEQ ID NO: 4.

E. coli JM 109 (Toyobo Co. Ltd.) was transformed with the plasmid SMBP-Kozak-pcDNA3.1/Zeo(+) poly-T free, and cultured overnight on a LB plate containing 50 µg/ml ampicillin to give transformants. The plasmids prepared from the transformants were cleaved with HindIII/XbaI to confirm that the SMBP-cDNA (about 2 kb) was inserted into the plasmid. Further, cleavage with ApaI confirmed the orientation of the inserted sequence.

EXAMPLE 4

Introduction of Human SMBP-Expression Plasmid into Animal Cells

CHO-k1 cells were plated into wells of a 6-well plate at $2 \times 10^5$ cells/well, and cultured for 24 hours in HAM's F-12 medium containing 10% fetal calf serum. The cells were transformed with pcDNA3.1/Zeo(+) (control), or each of human SMBP protein-expression plasmids, SMBP-pcDNA3.1/Zeo(+), SMBP-Kozak-pcDNA3.1/Zeo(+) and SMBP-Kozak-pcDNA3.1/Zeo(+) poly-T free as prepared in Examples 1 to 3, using lipids for gene incorporation (Lipofectamine; Gibco-BRL). From the fifth day after the transformations, the cells were cultured in HAM's F-12 medium containing 1.0 mg/ml Zeocin (Invitrogen) and 10% fetal calf serum, and cells wherein the plasmids were integrated in the chromosomes were selected.

EXAMPLE 5

Preparation of CHO Cellular Membrane Fractions Containing Human SMBP Protein

CHO cells containing the human SMBP protein obtained in Example 4 were cultured in an adherent manner in a culture dish having a diameter of 10 cm, and washed with phosphate buffered saline (PBS). To the cells, 5 ml of an ice-cooled, hypotonic homogenate buffer (10 mM Tris-HCl buffer, 1 mM EDTA, 0.5 mM PMSF or 1 mM AEBSF, 5 µg/ml aprotinin, 5 µg/ml leupeptin, pH7.4) was added, and the mixture was allowed to stand at 4° C. for 30 minutes, thereby destroying the cells due to the hypotonic condition. The destroyed material was homogenized by the pipetting, and the homogenate was centrifuged at 50000×g at 4° C. for about 30 minutes to give sediment of crude membrane fractions. The sediment was suspended in Tris-HCl buffered saline (Tris-HCl buffer, 154 mM sodium chloride, pH 7.4), and the suspension was stored at −80° C. Each time used, a portion of this was thawed. Protein concentration was determined by a Protein Assay Kit (Bio-Rad) wherein bovine serum albumin is used as a standard.

EXAMPLE 6

Measurement of Ligand-Binding Activity of Human SMBP Protein

Sugasawa et al. (Sugasawa, T. et al., *J. Biol. Chem.*, 272, 21244–21252 (1997)) reported that a ligand-binding reactivity of a human SMBP protein can be measured by use of 1 nM [$^{125}$I]-iodocyanopindolol (2000 Ci/mmol; Amersham) as a ligand, and, specifically, the ligand-binding reactivity of a human SMBP protein can be estimated by determining a nonspecific binding reactivity of iodocyanopindolol by use of $10^{-4}$M SM-11044, and subtracting the nonspecific binding reactivity from the binding reactivity. According to the instructions of this literature, a ligand-binding activity of a SMBP protein was measured. Further, the binding assay was conducted using a 96-well microtiter plate in order to accelerate the assay.

First, a 96-well Multiscreen plate (Millipore) in which a piece of glass fiber paper was placed on the bottom of the wells was supplemented with Tris-HCl buffered saline containing 0.3% polyethyleneimine (Sigma) (reconstituted to pH7.4 with 6N HCl), treated for 30 minutes or more, and washed aspirating with Tris-HCl buffered saline (pretreatment) by vacuum filtration.

Subsequently, 200 μl of Tris-HCl buffered saline containing 1 nM [$^{125}$I]-iodocyanopindolol and each cellular membrane fraction as prepared in Example 5 (50 μg of membrane protein) that had been incubated at 37° C. for 30 minutes was added to each well on the 96-well Multiscreen plate, and were aspirated by vacuum filtration. The cellular membrane fractions were harvested on the glass fiber paper, and washed four times by vacuum filtration with 200 μl of an ice-cooled Tris-HCl buffered saline. The amounts of [$^{125}$I]-iodocyanopindolol bound to the membrane fraction trapped on the paper were determined by a gamma counter to represent total bindings. Nonspecific bindings of [$^{125}$I]-iodocyanopindolol were determined by conducting incubations as mentioned above in the presence of $10^{-4}$ M SM-11044, and then conducting similar procedures to those mentioned above. In each case, the nonspecific binding was subtracted from the total binding to give a ligand-binding to SMBP (a specific binding). The results are shown in FIG. 1.

The membrane fraction of the CHO cells that were transformed with the expression plasmid introduced with the SMBP-cDNA described in WO 98/26065 (Example 1) (CHO-SMBP in FIG. 1), and the membrane fraction of the CHO cells that were transformed with the expression plasmid introduced with the Kozak sequence (Example 2) (CHO-SMBP-Kozak in FIG. 1) did not show any significant ligand-binding activities compared to the control (CHO-pcDNA3.1 in FIG. 1). Contrarily, the membrane fraction of the CHO cells that were transformed with the expression plasmid wherein the Kodak sequence was introduced, and the poly-T sequence was deleted (Example 3) (CHO-SMBP-Kozak-poly T free in FIG. 1) did show a significant ligand-binding activity compared to the control and to the CHO-SMBP cells before the deletion of the poly-T sequence. These results demonstrate that the deletion of the poly-T sequence causes an expression of a SMBP protein on the cellular membrane sufficient to show its ligand-binding activity.

EXAMPLE 7

Screening for Ligands of Human SMBP Protein

Two hundreds μl of Tris-HCl buffered saline containing 50 μg of membrane protein of the cellular membrane fraction of the CHO cells transformed with SMBP-Kozak-pcDNA3.1/Zeo(+) poly-T free (as prepared in Example 5) and 1 nM [$^{125}$I]-iodocyanopindolol is incubated at 37° C. for 30 minutes, and the reaction is added to each well on a 96-well Multiscreen plate that has been treated by a similar pretreatment to that in Example 6, and aspirated by vacuum filtration. Then, a similar treatment to that in Example 6 is conducted, and the amount of [$^{125}$I]-iodocyanopindolol bound to the membrane fraction trapped on the paper is determined by a gamma counter to give a binding, which represents binding A. Subsequently, the incubation as shown above is conducted in the presence of a test compound at a normal range of concentrations ($10^{-12}$–$10^{-4}$M), and then a similar procedure is conducted to give a binding, which represents binding B. A binding that is provided by use of $10^{-4}$M SM-11044 instead of a test compound represents binding C. When the value subtracted binding B from binding A is equivalent to one subtracted binding C from binding A, the test compound is estimated to have 100% SMBP-binding activity, and, when the value is the half, the compound is estimated to have the 50%. SMBP ligands thus selected are subjected to an assay as described in either *J. Biol. Chem.*, 272, 21244–21252 (1997), *Eur. J. Pharmacol.* 216, 207–215 (1992), or *Agents Actions* 37, 233–237 (1992). That procedure makes it possible to determine if the ligands have a SMBP-agonist activity, i.e., if the ligands down-regulate the contraction of intestine or if they inhibit the migration of eosinophils.

INDUSTRIAL APPLICABILITY

Cells that are transformed with an expression plasmid carrying a human SMBP cDNA wherein the polythymidine sequence is deleted according to the present invention can express a human SMBP to the extent that its ligand-binding activity can be measured. Accordingly, transformed cells containing a recombinant human SMBP, cellular membrane fractions thereof, or recombinant human SMBP isolated from said transformed cells or said cellular membrane fractions according to the present invention can be used to screen for ligands binding to a human SMBP. The screening systems of the present invention enable to efficiently discover human SMBP agonists or antagonists. Human tissues might be used in the screening system for discovering compounds binding to human SMBPs. However, when using human tissues, it is difficult to differentiate the intended ligands from those ligands to be bound to receptors other than the SMBPs existing at human tissues, such as human β1-, β2-, or β3-adrenergic receptors. The screening systems of the present invention make it possible to surely and efficiently select human SMBP agonists or antagonists, and, therefore, provides speedy development of pharmaceutical products such as pharmaceutical compositions for treating or preventing inflammatory diseases involving migration of eosinophils, antiasthmatic compositions, and pharmaceutical compositions for treating bowel diseases.

The invention claimed is:

1. A screening process for discovering an agonist or antagonist for human SMBP, which comprises
   1) contacting a transformed cell or the cellular membrane fraction thereof with a test compound, and
   2) measuring the SMBP-binding activity of a test compound to select a SMBP ligand among the test compounds,
   wherein the SMBP ligand is an agonist for human SMBP when it down-regulates the contraction of intestine or inhibits the migration of eosinophils, and the SMBP ligand is an antagonist for human SMBP when it shows the inverse activities, and
   wherein the transformed cell as defined in step 1) is obtained by culturing cells transformed with an expression vector carrying the DNA of any one of the following (a) to (e) under an appropriate condition:
   (a) an isolated DNA encoding a human SMBP, wherein said DNA comprises a nucleotide sequence of SEQ ID NO: 1, with the exception that a sequence comprising the polythymidine sequence from positions 1899 to 1935 of SEQ ID NO: 1 is deleted from a 3'-region from position 1875 in the nucleotide sequence of SEQ ID NO: 1; and the SMBP translation product of said isolated DNA is expressed at an elevated level compared to the level of expression of a DNA comprising unmodified SEQ ID NO: 1;
   (b) the DNA of (a), wherein said DNA comprises a nucleotide sequence of SEQ ID NO: 1, with the exception that the polythymidine sequence from positions 1899 to 1935 of SEQ ID NO: 1 is deleted;
   (c) the DNA of (a), wherein said DNA comprises a nucleotide sequence of SEQ ID NO: 1, with the exception that the nucleotide sequence from positions 1875 to 2072 of SEQ ID NO: 1 is deleted;
   (d) an isolated DNA which consists of the nucleotide sequence of SEQ ID NO: 3; and
   (e) the DNA of any one of (a), (b), or (c), wherein the surrounding sequence of the start codon is replaced with Kozac sequence of SEQ ID NO:5.

* * * * *

SEQUENCE LISTING

<160> NUMBER OF SEQ ID NOS: 7

<210> SEQ ID NO 1
<211> LENGTH: 2072
<212> TYPE: DNA
<213> ORGANISM: Homo sapiens

```
<220> FEATURE:
<221> NAME/KEY: CDS
<222> LOCATION: (49)..(1794)

<400> SEQUENCE: 1
ggatccacta gtaacggccg ccagtgtgct ggaattctgc agatctag atg cat gct       57
                                                    Met His Ala
                                                     1 cga gcg gcc gcc gcg ctg tgg ctg ctg ctg ctg ctg ccc cgg acc          105
Arg Ala Ala Ala Ala Leu Trp Leu Leu Leu Leu Leu Pro Arg Thr
      5                  10                  15 cgg gcg gac gag cac gaa cac acg tat caa gat aaa gag gaa gtt gtc    153
Arg Ala Asp Glu His Glu His Thr Tyr Gln Asp Lys Glu Glu Val Val
 20                  25                  30                  35 tta tgg atg aat act gtt ggg ccc tac cat aat cgt caa gaa aca tat    201
Leu Trp Met Asn Thr Val Gly Pro Tyr His Asn Arg Gln Glu Thr Tyr
                 40                  45                  50 aag tac ttt tca ctt cca ttc tgt gtg ggg tca aaa aaa agt atc agt    249
Lys Tyr Phe Ser Leu Pro Phe Cys Val Gly Ser Lys Lys Ser Ile Ser
             55                  60                  65 cat tac cat gaa act ctg gga gaa gca ctt caa ggg gtt gaa ttg gaa    297
His Tyr His Glu Thr Leu Gly Glu Ala Leu Gln Gly Val Glu Leu Glu
         70                  75                  80 ttt agt ggt ctg gat att aaa ttt aaa gat gat gtg atg cca gcc act    345
Phe Ser Gly Leu Asp Ile Lys Phe Lys Asp Asp Val Met Pro Ala Thr
 85                  90                  95 tac tgt gaa att gat tta gat aaa gaa aag aga gat gca ttt gta tat    393
Tyr Cys Glu Ile Asp Leu Asp Lys Glu Lys Arg Asp Ala Phe Val Tyr
100                 105                 110                 115 gcc ata aaa aat cat tac tgg tac cag atg tac ata gat gat tta cca    441
Ala Ile Lys Asn His Tyr Trp Tyr Gln Met Tyr Ile Asp Asp Leu Pro
                 120                 125                 130 ata tgg ggt att gtt ggt gag gct gat gaa aat gga gaa gat tac tat    489
Ile Trp Gly Ile Val Gly Glu Ala Asp Glu Asn Gly Glu Asp Tyr Tyr
             135                 140                 145 ctt tgg acc tat aaa aaa ctt gaa ata ggt ttt aat gga aat cga att    537
Leu Trp Thr Tyr Lys Lys Leu Glu Ile Gly Phe Asn Gly Asn Arg Ile
         150                 155                 160 gtt gat gtt aat cta act agt gaa gga aag gtg aaa ctg gtt cca aat    585
Val Asp Val Asn Leu Thr Ser Glu Gly Lys Val Lys Leu Val Pro Asn
165                 170                 175 act aaa atc cag atg tca tat tca gta aaa tgg aaa aag tca gat gtg    633
Thr Lys Ile Gln Met Ser Tyr Ser Val Lys Trp Lys Lys Ser Asp Val
180                 185                 190                 195 aaa ttt gaa gat cga ttt gac aaa tat ctt gat ccg tcc ttt ttt caa    681
Lys Phe Glu Asp Arg Phe Asp Lys Tyr Leu Asp Pro Ser Phe Phe Gln
                 200                 205                 210 cat cgg att cat tgg ttt tca att ttc aac tcc ttc atg atg gtg atc    729
His Arg Ile His Trp Phe Ser Ile Phe Asn Ser Phe Met Met Val Ile
             215                 220                 225 ttc ttg gtg ggc tta gtt tca atg att tta atg aga aca tta aga aaa    777
Phe Leu Val Gly Leu Val Ser Met Ile Leu Met Arg Thr Leu Arg Lys
         230                 235                 240 gat tat gct cgg tac agt aaa gag gaa gaa atg gat gat atg gat aga    825
Asp Tyr Ala Arg Tyr Ser Lys Glu Glu Glu Met Asp Asp Met Asp Arg
245                 250                 255 gac cta gga gat gaa tat gga tgg aaa cag gtg cat gga gat gta ttt    873
Asp Leu Gly Asp Glu Tyr Gly Trp Lys Gln Val His Gly Asp Val Phe
                 260                 265                 270                 275 aga cca tca agt cac cca ctg ata ttt tcc tct ctg att ggt tct gga    921
```

```
                Arg Pro Ser Ser His Pro Leu Ile Phe Ser Ser Leu Ile Gly Ser Gly
                            280                 285                 290 tgt cag ata ttt gct gtg tct ctc atc gtt att att gtt gca atg ata              969
Cys Gln Ile Phe Ala Val Ser Leu Ile Val Ile Ile Val Ala Met Ile
            295                 300                 305 gaa gat tta tat act gag agg gga tca atg ctc agt aca gcc ata ttt             1017
Glu Asp Leu Tyr Thr Glu Arg Gly Ser Met Leu Ser Thr Ala Ile Phe
            310                 315                 320 gtc tat gct gct acg tct cca gtg aat ggt tat ttt gga gga agt ctg             1065
Val Tyr Ala Ala Thr Ser Pro Val Asn Gly Tyr Phe Gly Gly Ser Leu
        325                 330                 335 tat gct aga caa gga gga agg aga tgg ata aag cag atg ttt att ggg             1113
Tyr Ala Arg Gln Gly Gly Arg Arg Trp Ile Lys Gln Met Phe Ile Gly
340                 345                 350                 355 gca ttc ctt atc cca gct atg gtg tgt ggc act gcc ttc ttc atc aat             1161
Ala Phe Leu Ile Pro Ala Met Val Cys Gly Thr Ala Phe Phe Ile Asn
                360                 365                 370 ttc ata gcc att tat tac cat gct tca aga gcc att cct ttt gga aca             1209
Phe Ile Ala Ile Tyr Tyr His Ala Ser Arg Ala Ile Pro Phe Gly Thr
            375                 380                 385 atg gtg gcc gtt tgt tgc atc tgt ttt ttt gtt att ctt cct cta aat             1257
Met Val Ala Val Cys Cys Ile Cys Phe Phe Val Ile Leu Pro Leu Asn
            390                 395                 400 ctt gtt ggt aca ata ctt ggc cga aat ctg tca ggt cag ccc aac ttt             1305
Leu Val Gly Thr Ile Leu Gly Arg Asn Leu Ser Gly Gln Pro Asn Phe
        405                 410                 415 cct tgt cgt gtc aat gct gtg cct cgt cct ata ccg gag aaa aaa tgg             1353
Pro Cys Arg Val Asn Ala Val Pro Arg Pro Ile Pro Glu Lys Lys Trp
420                 425                 430                 435 ttc atg gag cct gcg gtt att gtt tgc ctg ggt gga att tta cct ttt             1401
Phe Met Glu Pro Ala Val Ile Val Cys Leu Gly Gly Ile Leu Pro Phe
                440                 445                 450 ggt tca atc ttt att gaa atg tat ttc atc ttc acg tct ttc tgg gca             1449
Gly Ser Ile Phe Ile Glu Met Tyr Phe Ile Phe Thr Ser Phe Trp Ala
            455                 460                 465 tat aag atc tat tat gtc tat ggc ttc atg atg ctg gtg ctg gtt atc             1497
Tyr Lys Ile Tyr Tyr Val Tyr Gly Phe Met Met Leu Val Leu Val Ile
            470                 475                 480 ctg tgc att gtg act gtc tgt gtg act att gtg tgc aca tat ttt cta             1545
Leu Cys Ile Val Thr Val Cys Val Thr Ile Val Cys Thr Tyr Phe Leu
        485                 490                 495 cta aat gca gaa gat tac cgg tgg caa tgg aca agt ttt ctc tct gct             1593
Leu Asn Ala Glu Asp Tyr Arg Trp Gln Trp Thr Ser Phe Leu Ser Ala
500                 505                 510                 515 gca tca act gca atc tat gtt tac atg tat tcc ttt tac tat tat ttt             1641
Ala Ser Thr Ala Ile Tyr Val Tyr Met Tyr Ser Phe Tyr Tyr Tyr Phe
                520                 525                 530 ttc aaa aca aag atg tat ggc tta ttt caa aca tca ttt tac ttt gga             1689
Phe Lys Thr Lys Met Tyr Gly Leu Phe Gln Thr Ser Phe Tyr Phe Gly
            535                 540                 545 tat atg gcg gta ttt agc aca gcc ttg ggg ata atg tgt gga gcg att             1737
Tyr Met Ala Val Phe Ser Thr Ala Leu Gly Ile Met Cys Gly Ala Ile
            550                 555                 560 ggt tac atg gga aca agt gcc ttt gtc cga aaa atc tat act aat gtg             1785
Gly Tyr Met Gly Thr Ser Ala Phe Val Arg Lys Ile Tyr Thr Asn Val
        565                 570                 575 aaa att gac tagagaccca agaaacctg gaactttgga tcaatttctt               1834
Lys Ile Asp
580
```

-continued

```
tttcataggg gtggaacttg cacagcaaaa acaaacaaac gcaagaagag atttgggctt    1894 taacttttt  tttttttttt tttttttttt tttttttttt tacgaatgag gcaatttatt    1954
aacccagcat ggtttgttct aatgcttctt gttggcagct gccacctgtc cggcgattct    2014
gtccagatct ctttgtccct gaggtgtcag tttgcggccg ctcgagcatg catctaga     2072
```

<210> SEQ ID NO 2
<211> LENGTH: 582
<212> TYPE: PRT
<213> ORGANISM: Homo sapiens

<400> SEQUENCE: 2

```
Met His Ala Arg Ala Ala Ala Leu Trp Leu Leu Leu Leu Leu Leu
1               5                   10                  15

Pro Arg Thr Arg Ala Asp Glu His Glu His Thr Tyr Gln Asp Lys Glu
            20                  25                  30

Glu Val Val Leu Trp Met Asn Thr Val Gly Pro Tyr His Asn Arg Gln
        35                  40                  45

Glu Thr Tyr Lys Tyr Phe Ser Leu Pro Phe Cys Val Gly Ser Lys Lys
    50                  55                  60

Ser Ile Ser His Tyr His Glu Thr Leu Gly Glu Ala Leu Gln Gly Val
65                  70                  75                  80

Glu Leu Glu Phe Ser Gly Leu Asp Ile Lys Phe Lys Asp Asp Val Met
                85                  90                  95

Pro Ala Thr Tyr Cys Glu Ile Asp Leu Asp Lys Glu Lys Arg Asp Ala
            100                 105                 110

Phe Val Tyr Ala Ile Lys Asn His Tyr Trp Tyr Gln Met Tyr Ile Asp
        115                 120                 125

Asp Leu Pro Ile Trp Gly Ile Val Gly Glu Ala Asp Glu Asn Gly Glu
    130                 135                 140

Asp Tyr Tyr Leu Trp Thr Tyr Lys Lys Leu Glu Ile Gly Phe Asn Gly
145                 150                 155                 160

Asn Arg Ile Val Asp Val Asn Leu Thr Ser Glu Gly Lys Val Lys Leu
                165                 170                 175

Val Pro Asn Thr Lys Ile Gln Met Ser Tyr Ser Val Lys Trp Lys Lys
            180                 185                 190

Ser Asp Val Lys Phe Glu Asp Arg Phe Asp Lys Tyr Leu Asp Pro Ser
        195                 200                 205

Phe Phe Gln His Arg Ile His Trp Phe Ser Ile Phe Asn Ser Phe Met
    210                 215                 220

Met Val Ile Phe Leu Val Gly Leu Val Ser Met Ile Leu Met Arg Thr
225                 230                 235                 240

Leu Arg Lys Asp Tyr Ala Arg Tyr Ser Lys Glu Glu Met Asp Asp
                245                 250                 255

Met Asp Arg Asp Leu Gly Asp Glu Tyr Gly Trp Lys Gln Val His Gly
            260                 265                 270

Asp Val Phe Arg Pro Ser Ser His Pro Leu Ile Phe Ser Ser Leu Ile
        275                 280                 285

Gly Ser Gly Cys Gln Ile Phe Ala Val Ser Leu Ile Val Ile Ile Val
    290                 295                 300

Ala Met Ile Glu Asp Leu Tyr Thr Glu Arg Gly Ser Met Leu Ser Thr
305                 310                 315                 320

Ala Ile Phe Val Tyr Ala Ala Thr Ser Pro Val Asn Gly Tyr Phe Gly
                325                 330                 335
```

```
Gly Ser Leu Tyr Ala Arg Gln Gly Gly Arg Arg Trp Ile Lys Gln Met
            340                 345                 350

Phe Ile Gly Ala Phe Leu Ile Pro Ala Met Val Cys Gly Thr Ala Phe
            355                 360                 365

Phe Ile Asn Phe Ile Ala Ile Tyr Tyr His Ala Ser Arg Ala Ile Pro
            370                 375                 380

Phe Gly Thr Met Val Ala Val Cys Cys Ile Cys Phe Val Ile Leu
385                 390                 395                 400

Pro Leu Asn Leu Val Gly Thr Ile Leu Gly Arg Asn Leu Ser Gly Gln
            405                 410                 415

Pro Asn Phe Pro Cys Arg Val Asn Ala Val Pro Arg Pro Ile Pro Glu
            420                 425                 430

Lys Lys Trp Phe Met Glu Pro Ala Val Ile Val Cys Leu Gly Gly Ile
            435                 440                 445

Leu Pro Phe Gly Ser Ile Phe Ile Glu Met Tyr Phe Ile Phe Thr Ser
            450                 455                 460

Phe Trp Ala Tyr Lys Ile Tyr Tyr Val Tyr Gly Phe Met Met Leu Val
465                 470                 475                 480

Leu Val Ile Leu Cys Ile Val Thr Val Cys Val Thr Ile Val Cys Thr
            485                 490                 495

Tyr Phe Leu Leu Asn Ala Glu Asp Tyr Arg Trp Gln Trp Thr Ser Phe
            500                 505                 510

Leu Ser Ala Ala Ser Thr Ala Ile Tyr Val Tyr Met Tyr Ser Phe Tyr
            515                 520                 525

Tyr Tyr Phe Phe Lys Thr Lys Met Tyr Gly Leu Phe Gln Thr Ser Phe
            530                 535                 540

Tyr Phe Gly Tyr Met Ala Val Phe Ser Thr Ala Leu Gly Ile Met Cys
545                 550                 555                 560

Gly Ala Ile Gly Tyr Met Gly Thr Ser Ala Phe Val Arg Lys Ile Tyr
            565                 570                 575

Thr Asn Val Lys Ile Asp
            580

<210> SEQ ID NO 3
<211> LENGTH: 1827
<212> TYPE: DNA
<213> ORGANISM: Homo sapiens
<220> FEATURE:
<221> NAME/KEY: CDS
<222> LOCATION: (11)..(1747)

<400> SEQUENCE: 3
agcttccacc atg gcg gcc gcc gcg ctg tgg ctg ctg ctg ctg ctg          49
           Met Ala Ala Ala Ala Leu Trp Leu Leu Leu Leu Leu Leu
             1               5                  10 ccc cgg acc cgg gcg gac gag cac gaa cac acg tat caa gat aaa gag    97
Pro Arg Thr Arg Ala Asp Glu His Glu His Thr Tyr Gln Asp Lys Glu
         15                  20                  25 gaa gtt gtc tta tgg atg aat act gtt ggg ccc tac cat aat cgt caa   145
Glu Val Val Leu Trp Met Asn Thr Val Gly Pro Tyr His Asn Arg Gln
 30                  35                  40                  45 gaa aca tat aag tac ttt tca ctt cca ttc tgt gtg ggg tca aaa aaa   193
Glu Thr Tyr Lys Tyr Phe Ser Leu Pro Phe Cys Val Gly Ser Lys Lys
                 50                  55                  60 agt atc agt cat tac cat gaa act ctg gga gaa gca ctt caa ggg gtt   241
Ser Ile Ser His Tyr His Glu Thr Leu Gly Glu Ala Leu Gln Gly Val
             65                  70                  75
```

-continued

| | |
|---|---|
| gaa ttg gaa ttt agt ggt ctg gat att aaa ttt aaa gat gat gtg atg<br>Glu Leu Glu Phe Ser Gly Leu Asp Ile Lys Phe Lys Asp Asp Val Met<br>      80                          85                        90 | 289 |
| cca gcc act tac tgt gaa att gat tta gat aaa gaa aag aga gat gca<br>Pro Ala Thr Tyr Cys Glu Ile Asp Leu Asp Lys Glu Lys Arg Asp Ala<br>      95                        100                     105 | 337 |
| ttt gta tat gcc ata aaa aat cat tac tgg tac cag atg tac ata gat<br>Phe Val Tyr Ala Ile Lys Asn His Tyr Trp Tyr Gln Met Tyr Ile Asp<br>110                      115                     120                 125 | 385 |
| gat tta cca ata tgg ggt att gtt ggt gag gct gat gaa aat gga gaa<br>Asp Leu Pro Ile Trp Gly Ile Val Gly Glu Ala Asp Glu Asn Gly Glu<br>                      130                     135                 140 | 433 |
| gat tac tat ctt tgg acc tat aaa aaa ctt gaa ata ggt ttt aat gga<br>Asp Tyr Tyr Leu Trp Thr Tyr Lys Lys Leu Glu Ile Gly Phe Asn Gly<br>             145                     150                     155 | 481 |
| aat cga att gtt gat gtt aat cta act agt gaa gga aag gtg aaa ctg<br>Asn Arg Ile Val Asp Val Asn Leu Thr Ser Glu Gly Lys Val Lys Leu<br>        160                     165                     170 | 529 |
| gtt cca aat act aaa atc cag atg tca tat tca gta aaa tgg aaa aag<br>Val Pro Asn Thr Lys Ile Gln Met Ser Tyr Ser Val Lys Trp Lys Lys<br>175                      180                     185 | 577 |
| tca gat gtg aaa ttt gaa gat cga ttt gac aaa tat ctt gat ccg tcc<br>Ser Asp Val Lys Phe Glu Asp Arg Phe Asp Lys Tyr Leu Asp Pro Ser<br>190                      195                     200                 205 | 625 |
| ttt ttt caa cat cgg att cat tgg ttt tca att ttc aac tcc ttc atg<br>Phe Phe Gln His Arg Ile His Trp Phe Ser Ile Phe Asn Ser Phe Met<br>                      210                     215                 220 | 673 |
| atg gtg atc ttc ttg gtg ggc tta gtt tca atg att tta atg aga aca<br>Met Val Ile Phe Leu Val Gly Leu Val Ser Met Ile Leu Met Arg Thr<br>                225                     230                     235 | 721 |
| tta aga aaa gat tat gct cgg tac agt aaa gag gaa gaa atg gat gat<br>Leu Arg Lys Asp Tyr Ala Arg Tyr Ser Lys Glu Glu Glu Met Asp Asp<br>       240                     245                     250 | 769 |
| atg gat aga gac cta gga gat gaa tat gga tgg aaa cag gtg cat gga<br>Met Asp Arg Asp Leu Gly Asp Glu Tyr Gly Trp Lys Gln Val His Gly<br>255                      260                     265 | 817 |
| gat gta ttt aga cca tca agt cac cca ctg ata ttt tcc tct ctg att<br>Asp Val Phe Arg Pro Ser Ser His Pro Leu Ile Phe Ser Ser Leu Ile<br>270                      275                     280                 285 | 865 |
| ggt tct gga tgt cag ata ttt gct gtg tct ctc atc gtt att att gtt<br>Gly Ser Gly Cys Gln Ile Phe Ala Val Ser Leu Ile Val Ile Ile Val<br>                290                     295                     300 | 913 |
| gca atg ata gaa gat tta tat act gag agg gga tca atg ctc agt aca<br>Ala Met Ile Glu Asp Leu Tyr Thr Glu Arg Gly Ser Met Leu Ser Thr<br>             305                     310                     315 | 961 |
| gcc ata ttt gtc tat gct gct acg tct cca gtg aat ggt tat ttt gga<br>Ala Ile Phe Val Tyr Ala Ala Thr Ser Pro Val Asn Gly Tyr Phe Gly<br>          320                     325                     330 | 1009 |
| gga agt ctg tat gct aga caa gga gga agg aga tgg ata aag cag atg<br>Gly Ser Leu Tyr Ala Arg Gln Gly Gly Arg Arg Trp Ile Lys Gln Met<br>335                      340                     345 | 1057 |
| ttt att ggg gca ttc ctt atc cca gct atg gtg tgt ggc act gcc ttc<br>Phe Ile Gly Ala Phe Leu Ile Pro Ala Met Val Cys Gly Thr Ala Phe<br>350                      355                     360                 365 | 1105 |
| ttc atc aat ttc ata gcc att tat tac cat gct tca aga gcc att cct<br>Phe Ile Asn Phe Ile Ala Ile Tyr Tyr His Ala Ser Arg Ala Ile Pro<br>                      370                     375                 380 | 1153 |
| ttt gga aca atg gtg gcc gtt tgt tgc atc tgt ttt ttt gtt att ctt<br>Phe Gly Thr Met Val Ala Val Cys Cys Ile Cys Phe Phe Val Ile Leu<br>                385                     390                     395 | 1201 |

```
cct cta aat ctt gtt ggt aca ata ctt ggc cga aat ctg tca ggt cag          1249
Pro Leu Asn Leu Val Gly Thr Ile Leu Gly Arg Asn Leu Ser Gly Gln
            400                 405                 410 ccc aac ttt cct tgt cgt gtc aat gct gtg cct cgt cct ata ccg gag          1297
Pro Asn Phe Pro Cys Arg Val Asn Ala Val Pro Arg Pro Ile Pro Glu
        415                 420                 425 aaa aaa tgg ttc atg gag cct gcg gtt att gtt tgc ctg ggt gga att          1345
Lys Lys Trp Phe Met Glu Pro Ala Val Ile Val Cys Leu Gly Gly Ile
430                 435                 440                 445 tta cct ttt ggt tca atc ttt att gaa atg tat ttc atc ttc acg tct          1393
Leu Pro Phe Gly Ser Ile Phe Ile Glu Met Tyr Phe Ile Phe Thr Ser
                450                 455                 460 ttc tgg gca tat aag atc tat tat gtc tat ggc ttc atg atg ctg gtg          1441
Phe Trp Ala Tyr Lys Ile Tyr Tyr Val Tyr Gly Phe Met Met Leu Val
            465                 470                 475 ctg gtt atc ctg tgc att gtg act gtc tgt gtg act att gtg tgc aca          1489
Leu Val Ile Leu Cys Ile Val Thr Val Cys Val Thr Ile Val Cys Thr
        480                 485                 490 tat ttt cta cta aat gca gaa gat tac cgg tgg caa tgg aca agt ttt          1537
Tyr Phe Leu Leu Asn Ala Glu Asp Tyr Arg Trp Gln Trp Thr Ser Phe
495                 500                 505 ctc tct gct gca tca act gca atc tat gtt tac atg tat tcc ttt tac          1585
Leu Ser Ala Ala Ser Thr Ala Ile Tyr Val Tyr Met Tyr Ser Phe Tyr
510                 515                 520                 525 tac tat ttt ttc aaa aca aag atg tat ggc tta ttt caa aca tca ttt          1633
Tyr Tyr Phe Phe Lys Thr Lys Met Tyr Gly Leu Phe Gln Thr Ser Phe
                530                 535                 540 tac ttt gga tat atg gcg gta ttt agc aca gcc ttg ggg ata atg tgt          1681
Tyr Phe Gly Tyr Met Ala Val Phe Ser Thr Ala Leu Gly Ile Met Cys
            545                 550                 555 gga gcg att ggt tac atg gga aca agt gcc ttt gtc cga aaa atc tat          1729
Gly Ala Ile Gly Tyr Met Gly Thr Ser Ala Phe Val Arg Lys Ile Tyr
        560                 565                 570 act aat gtg aaa att gac tagagaccca agaaaacctg aactttgga                  1777
Thr Asn Val Lys Ile Asp
    575 tcaatttctt tttcataggg gtggaacttg cacagcaaaa acaaacaaac                   1827

<210> SEQ ID NO 4
<211> LENGTH: 579
<212> TYPE: PRT
<213> ORGANISM: Homo sapiens

<400> SEQUENCE: 4

Met Ala Ala Ala Leu Trp Leu Leu Leu Leu Leu Pro Arg Thr
1               5                   10                  15

Arg Ala Asp Glu His Glu His Thr Tyr Gln Asp Lys Glu Val Val
            20                  25                  30

Leu Trp Met Asn Thr Val Gly Pro Tyr His Asn Arg Gln Glu Thr Tyr
        35                  40                  45

Lys Tyr Phe Ser Leu Pro Phe Cys Val Gly Ser Lys Lys Ser Ile Ser
50                  55                  60

His Tyr His Glu Thr Leu Gly Glu Ala Leu Gln Gly Val Glu Leu Glu
65                  70                  75                  80

Phe Ser Gly Leu Asp Ile Lys Phe Lys Asp Asp Val Met Pro Ala Thr
                85                  90                  95

Tyr Cys Glu Ile Asp Leu Asp Lys Glu Lys Arg Asp Ala Phe Val Tyr
            100                 105                 110
```

```
Ala Ile Lys Asn His Tyr Trp Tyr Gln Met Tyr Ile Asp Asp Leu Pro
            115                 120                 125

Ile Trp Gly Ile Val Gly Glu Ala Asp Glu Asn Gly Glu Asp Tyr Tyr
        130                 135                 140

Leu Trp Thr Tyr Lys Lys Leu Glu Ile Gly Phe Asn Gly Asn Arg Ile
145                 150                 155                 160

Val Asp Val Asn Leu Thr Ser Glu Gly Lys Val Lys Leu Val Pro Asn
                165                 170                 175

Thr Lys Ile Gln Met Ser Tyr Ser Val Lys Trp Lys Ser Asp Val
            180                 185                 190

Lys Phe Glu Asp Arg Phe Asp Lys Tyr Leu Asp Pro Ser Phe Phe Gln
        195                 200                 205

His Arg Ile His Trp Phe Ser Ile Phe Asn Ser Phe Met Met Val Ile
        210                 215                 220

Phe Leu Val Gly Leu Val Ser Met Ile Leu Met Arg Thr Leu Arg Lys
225                 230                 235                 240

Asp Tyr Ala Arg Tyr Ser Lys Glu Glu Met Asp Asp Met Asp Arg
                245                 250                 255

Asp Leu Gly Asp Glu Tyr Gly Trp Lys Gln Val His Gly Asp Val Phe
            260                 265                 270

Arg Pro Ser Ser His Pro Leu Ile Phe Ser Ser Leu Ile Gly Ser Gly
        275                 280                 285

Cys Gln Ile Phe Ala Val Ser Leu Ile Val Ile Ile Val Ala Met Ile
        290                 295                 300

Glu Asp Leu Tyr Thr Glu Arg Gly Ser Met Leu Ser Thr Ala Ile Phe
305                 310                 315                 320

Val Tyr Ala Ala Thr Ser Pro Val Asn Gly Tyr Phe Gly Gly Ser Leu
                325                 330                 335

Tyr Ala Arg Gln Gly Gly Arg Arg Trp Ile Lys Gln Met Phe Ile Gly
            340                 345                 350

Ala Phe Leu Ile Pro Ala Met Val Cys Gly Thr Ala Phe Phe Ile Asn
        355                 360                 365

Phe Ile Ala Ile Tyr Tyr His Ala Ser Arg Ala Ile Pro Phe Gly Thr
370                 375                 380

Met Val Ala Val Cys Cys Ile Cys Phe Val Ile Leu Pro Leu Asn
385                 390                 395                 400

Leu Val Gly Thr Ile Leu Gly Arg Asn Leu Ser Gly Gln Pro Asn Phe
                405                 410                 415

Pro Cys Arg Val Asn Ala Val Pro Arg Pro Ile Pro Glu Lys Lys Trp
            420                 425                 430

Phe Met Glu Pro Ala Val Ile Val Cys Leu Gly Gly Ile Leu Pro Phe
        435                 440                 445

Gly Ser Ile Phe Ile Glu Met Tyr Phe Ile Phe Thr Ser Phe Trp Ala
        450                 455                 460

Tyr Lys Ile Tyr Tyr Val Tyr Gly Phe Met Met Leu Val Leu Val Ile
465                 470                 475                 480

Leu Cys Ile Val Thr Val Cys Val Thr Ile Val Cys Thr Tyr Phe Leu
                485                 490                 495

Leu Asn Ala Glu Asp Tyr Arg Trp Gln Trp Thr Ser Phe Leu Ser Ala
            500                 505                 510

Ala Ser Thr Ala Ile Tyr Val Tyr Met Tyr Ser Phe Tyr Tyr Phe
        515                 520                 525
```

-continued

```
Phe Lys Thr Lys Met Tyr Gly Leu Phe Gln Thr Ser Phe Tyr Phe Gly
    530             535             540

Tyr Met Ala Val Phe Ser Thr Ala Leu Gly Ile Met Cys Gly Ala Ile
545             550             555             560

Gly Tyr Met Gly Thr Ser Ala Phe Val Arg Lys Ile Tyr Thr Asn Val
                565             570             575

Lys Ile Asp

<210> SEQ ID NO 5
<211> LENGTH: 7
<212> TYPE: DNA
<213> ORGANISM: Artificial Sequence
<220> FEATURE:
<223> OTHER INFORMATION: Kozak's Consensus Sequence

<400> SEQUENCE: 5 accatgg                                                           7

<210> SEQ ID NO 6
<211> LENGTH: 15
<212> TYPE: DNA
<213> ORGANISM: Artificial Sequence
<220> FEATURE:
<223> OTHER INFORMATION: Adapter containing the Kozak's Consensus
      Sequence

<400> SEQUENCE: 6
agcttccacc atggc                                                 15

<210> SEQ ID NO 7
<211> LENGTH: 15
<212> TYPE: DNA
<213> ORGANISM: Artificial Sequence
<220> FEATURE:
<223> OTHER INFORMATION: Adapter containing the Kozak's Consensus
      Sequence (listed as 5' to 3')

<400> SEQUENCE: 7
ggccgccatg gtgga                                                 15
```